(12) United States Patent  (10) Patent No.: US 7,973,056 B2
Nagayama  (45) Date of Patent: Jul. 5, 2011

(54) TRIAZOLE DERIVATIVE OR SALT THEREOF (75) Inventor: Takashi Nagayama, Kanagawa (JP)

(73) Assignee: Fujifilm Finechemicals Co., Ltd, Kanagawa (JP)

( * ) Notice: Subject to any disclaimer, the term of this patent is extended or adjusted under 35 U.S.C. 154(b) by 243 days.

(21) Appl. No.: 12/474,808

(22) Filed: May 29, 2009

(65) Prior Publication Data

US 2009/0299071 A1  Dec. 3, 2009

(30) Foreign Application Priority Data

May 30, 2008  (JP) .................. 2008-143232

(51) Int. Cl.
C07D 401/14 (2006.01)
A61K 31/4545 (2006.01)
A61K 31/444 (2006.01)

(52) U.S. Cl. ......... 514/318; 514/333; 546/194; 546/256

(58) Field of Classification Search .......... 514/318, 514/333; 546/194, 256
See application file for complete search history.

(56) References Cited

U.S. PATENT DOCUMENTS

| | | |
|---|---|---|
| 2,802,005 A | 8/1957 | Heidelberger |
| 2,908,611 A | 10/1959 | Dutcher |
| 4,144,346 A | 3/1979 | Heeres |
| 4,223,036 A | 9/1980 | Heeres |
| 4,335,125 A | 6/1982 | Heeres |
| 4,358,449 A | 11/1982 | Heeres |
| 4,404,216 A | 9/1983 | Richardson |
| 5,278,175 A | 1/1994 | Ray |
| 5,567,817 A | 10/1996 | Ray |
| 5,773,443 A | 6/1998 | Ray |

FOREIGN PATENT DOCUMENTS

| | | |
|---|---|---|
| EP | 0440372 A | 8/1991 |
| JP | 53-095973 A | 8/1978 |
| JP | 58-032868 A | 2/1983 |
| JP | 10-045750 A | 2/1998 |

OTHER PUBLICATIONS

Extended European Search Report dated Aug. 11, 2009.

Primary Examiner — Joseph Kosack
Assistant Examiner — Matthew P Coughlin
(74) Attorney, Agent, or Firm — Sughrue Mion, PLLC

(57) ABSTRACT

A triazole derivative or pharmaceutically acceptable salt thereof is provided, the triazole derivative being represented by formula (I):

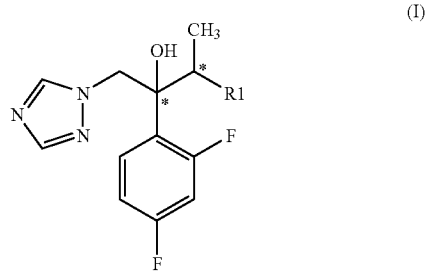

(I)

wherein * represents an asymmetric carbon and takes R configuration or S configuration; and R1 represents a structure represented by formula (II) or (III):

(II)

I-1

(III)

-----represents single bond or double bond wherein Y represents a hydrogen atom or an oxygen atom; and R2 and R3 each independently represent a hydrogen atom, an alkyl group, an aryl group, an alkoxy group, a formyl group, a carboxyl group, an alkylcarbonyl group, an arylcarbonyl group, an alkoxycarbonyl group, a carbamoyl group, an amino group, an alkylcarbonylamino group, an arylcarbonylamino group, a cyano group, a nitro group or a halogen atom.

7 Claims, 2 Drawing Sheets

FIG. 1D
Fluconazole

TRIAZOLE DERIVATIVE OR SALT THEREOF

BACKGROUND OF THE INVENTION

1. Field of the Invention

This invention relates to a pharmaceutical, particularly a triazole derivative useful as an antifungal agent.

2. Description of the Related Art

Based on the infected regions, mycosis is roughly divided into superficial mycosis such as marginated eczema, psoriasis, various types of trichophytosis, skin *Candida* infection and the like and deep mycosis such as fungal meningitis, fungal respiratory organ infection, fungemia, mycosis of urinary tract and the like. The later cases among them are infections in which the whole body organs and tissues are affected by fungi, and many of them have a particularly increasing tendency in recent years due to the use of chemotherapeutic agents, frequent use of immunosuppressants by organ transplantation, lowering of immunity in the living body by AIDS infection and the like. As the deep mycosis, aspergillosis, *Cryptococcosis*, candidiasis, zygomycosis and the like can be exemplified, but drugs effective for these are rare. As the therapeutic drugs to be used, a polyene macrolide antibiotic substance Amphotericin B (U.S. Pat. No. 2,908,611) and a fluoropyrimidine compound Flucytosine (U.S. Pat. No. 2,802,005) are typical. However, these drugs have problems in that side effects are strong, resistant strains are apt to appear, and the like.

On the other hand, a great number of azole system compounds having antifungal actions have been developed and put on the market in recent years. These compounds have actions to inhibit metabolic enzymes useful in biosynthesizing ergosterol which is necessary for keeping cell membrane functions, and for example, Fluconazole (JP-A-58-32868), Ketoconazole (JP-A-53-95973), Voriconazol (European Patent Application No. 440372) and the like are known. However, it is hard to say that these are sufficient from the viewpoint of antifungal spectrum, pharmacokinetics, side effects and the like. In order to solve these problems, concern has been directed toward the development of a compound which is excellent in safety and also has further strong antifungal activity.

SUMMARY OF THE INVENTION

As a result of carrying out many years of intensive studies, the inventors have found a novel azole system compound having a strong antifungal activity, which is characterized by the possession of a bipyridine derivative, a reduced form of the bipyridine derivative or a pyridylpyridone derivative, and thereby accomplished the invention.

(1) A triazole derivative represented by formula (I) or pharmaceutically acceptable salt thereof:

(I)

wherein,

\* represents an asymmetric carbon and takes R configuration or S configuration; and R1 represents a structure represented by formula (II) or (III):

-----represents single bond or double bond wherein,

Y represents a hydrogen atom or an oxygen atom; and

R2 and R3 each independently represent a hydrogen atom, an alkyl group, an aryl group, an alkoxy group, a formyl group, a carboxyl group, an alkylcarbonyl group, an arylcarbonyl group, an alkoxycarbonyl group, a carbamoyl group, an amino group, an alkylcarbonylamino group, an arylcarbonylamino group, a cyano group, a nitro group or a halogen atom.

(2) The triazole derivative or pharmaceutically acceptable salt thereof as described in (1) above, wherein R2 represents a hydrogen atom, an alkyl group having from 1 to 8 carbon atoms, an alkoxyl group having from 1 to 8 carbon atoms, a cyano group or a halogen atom; and R3 represents a hydrogen atom, an alkyl group having from 1 to 8 carbon atoms, an alkoxyl group having from 1 to 8 carbon atoms, a cyano group or a halogen atom.

(3) The triazole derivative or pharmaceutically acceptable salt thereof as described in (2) above, wherein R2 represents a hydrogen atom, an alkyl group having from 1 to 4 carbon atoms, a cyano group, a chlorine atom or a fluorine atom; and R3 represents a hydrogen atom, an alkyl group having from 1 to 4 carbon atoms, an alkoxyl group having from 1 to 4 carbon atoms, a cyano group, a chlorine atom ox a fluorine atom.

(4) The triazole derivative or pharmaceutically acceptable salt thereof as described in (3) above, wherein R2 represents a hydrogen atom or a methyl group; and R3 represents a hydrogen atom, an alkyl group having from 1 to 4 carbon atoms, a chlorine atom or a fluorine atom.

(5) The triazole derivative or pharmaceutically acceptable salt thereof as described in any one of (1) to (4) above, wherein the triazole derivative represented by formula (I) is a structure represented by formula (I'):

(I')

wherein R1 has the same meaning as R1 in formula (I).

(6) The triazole derivative or pharmaceutically acceptable salt thereof as described in any one of (1) to (5) above, wherein R1 represents a structure represented by formula (III-1) or (III-2):

wherein R2 and R3 in formulae (III-1) and (III-2) are the same as R2 and R3 in formulae (II) and (III).

(7) A pharmaceutical composition, comprising:
the triazole derivative or pharmaceutically acceptable salt thereof as described in any one of (1) to (6) above.

(8) The pharmaceutical composition as described in (7) above, which is an antifungal agent.

BRIEF DESCRIPTION OF THE DRAWINGS

FIGS. 1A to 1D are graphs showing survival rates in mouse systemic infection models in Test Example 2 in which FIG. 1A shows the results when using compound I-1, FIG. 1B shows the results when using compound I-3, FIG. 1C shows the results when using compound I-6, and FIG. 1D shows the results when using Fluconazole.

DETAILED DESCRIPTION OF THE INVENTION

The following describes the invention further in detail.

In the formula (I), R1 represents a structure represented by a formula (II) or (III).

In this connections the dotted line in the formula (III) represents a single bond or double bond in the 6-membered heterocyclic structure consisting of one nitrogen atom and five carbon atoms.

As illustrative structure of R1, for example, 2,2'-bipyridin-6'-yloxy group, 2,3'-bipyridin-6'-yloxy group, 2,4'-bipyridin-2'-yloxy group, 2,3'-bipyridin-2'-yloxy group, 3',6'-dihydro-2,2'-bipyridin-1'(2'H)-yl group, 3',6'-dihydro-2,3'-bipyridin-1'(2'H)-yl group, 3',6'-dihydro-2,4'-bipyridin-1'(2'H)-yl group, 2-pyridin-2-ylpiperidin-1-yl group, 3-pyridin-2-ylpiperidin-1-yl group, 4-pyridin-2-ylpiperidin-1-yl group, 6'-oxo-2,2'-bipyridin-1'-yl group, 6'-oxo-2,3'-bipyridin-1'-yl group, 2'-oxo-2,4'-bipyridin-1'-yl group and 2'-oxo-2,5'-bipyridin-1'-yl group can be exemplified. Preferred among these are 2,4'-bipyridin-2'-yloxy group, 3',6'-dihydro-2,3'-bipyridin-1'(2'H)-yl group, 3',6'-dihydro-2,4'-bipyridin-1'(2'H)-yl group, 3-pyridin-2-ylpiperidin-1-yl group, 4-pyridin-2-ylpiperidin-1-yl group and 2'-oxo-2,4'-bipyridin-1'-yl group, of which further preferred is 3',6'-dihydro-2,4'-bipyridin-1'(2'H)-yl group as described by following formula (III-1) or 4-pyridin-2-ylpiperidin-1-yl group as described by following formula (III-2). R2 and R3 in formulae (III-1) and (III-2) are the same as R2 and R3 in formulae (II) and (III).

As the alkyl group represented by R2 and R3 in the formulae (II), (III), (III-1) and (III-2), methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclobutyl, cyclopentyl, cyclohexyl, cycloheptyl, cyclooctyl, cyclononyl, cyclodecyl and the like straight, branched or cyclic alkyl groups having from 1 to 20 carbon atoms can for example be cited.

As the aryl group represented by R2 and R3, phenyl, naphthyl and the like monocyclic or bicyclic aryl groups having from 6 to 10 carbon atoms can for example be cited.

As the alkoxy group represented by R2 and R3, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy and the like alkoxy groups having from 1 to 20 carbon atoms can for example be cited.

As the alkylcarbonyl group represented by R2 and R3, acetyl, propionyl, butyryl, valeryl, decanoyl, tetradecanoyl and the like carbonyl groups substituted with an alkyl group having from 1 to 20 carbon atoms can for example be cited.

As the arylcarbonyl group represented by R2 and R3, benzoyl, naphthoyl and the like carbonyl groups substituted with a monocyclic or bicyclic aryl group having from 6 to 10 carbon atoms can for example be cited.

As the alkoxycarbonyl group represented by R2 and R3, methoxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl, eicosyloxycarbonyl and the like carbonyl groups substituted with an alkoxyl group having from 1 to 20 carbon atoms can for example be cited.

As the carbamoyl group represented by R2 and R3, unsubstituted carbamoyl group; N-methylcarbamoyl, N-ethylcarbamoyl, N-(tert-butyl) carbamoyl, N-hexylcarbamoyl, N-octylcarbamoyl, N-dodecylcarbamoyl, N-octadecylcarbamoyl, N-phenylcarbamoyl, N-naphthylcarbamoyl and the like mono-substituted carbamoyl groups; and N,N-dimethylcarbamoyl, N,N-diethylcarbamoyl, N,N-dihexylcarbamoyl, N,N-didodecylcarbamoyl, N-methyl-N-ethylcarbamoyl, N-methyl-N-phenylcarbamoyl, N,N-diphenylcarbamoyl and the like di-substituted carbamoyl groups can for example be cited.

As the amino group represented by R2 and R3, unsubstituted amino group; N-methylamino, N-ethylamino, N-propylamino, N-butylamino, N-hexylamino, N-decylamino, N-tetradecylamino, N-octadecylamino, N-phenylamino, N-naphthylamino and the like mono-substituted amino groups; and N,N-diethylamino, N,N-diethylamino, N,N-diheptylamino, N,N-dioctylamino, N,N-didodecylamino, N,N-dioctadecylamino, N,N-diphenylamino, N-methyl-N-ethylamino, N-ethyl-N-butylamino, N-methyl-N-phenylamino, N-ethyl-N-naphthylamino and the like di-substituted amino groups can for example be cited.

As the alkylcarbonylamino group represented by R2 and R3, acetylamino, ethylcarbonylamino, isopropylcarbonylamino, tert-butylcarbonylamino, n-hexylcarbonylamino, n-octylcarbonylamino, n-dodecylcarbonylamino, n-hexadecylcarbonylamino and the like carbonylamino groups substituted with an alkyl group having from 1 to 20 carbon atoms can for example be cited.

As the arylcarbonylamino group represented by R2 and R3, benzoylamino, naphthoylamino and the like carbonylamino groups substituted with a monocyclic or bicyclic axyl group having from 6 to 10 carbon atoms can for example be cited.

As the halogen atom represented by R2 and R3, chlorine atom, bromine atom, iodine atom or fluorine atom can be cited.

The substituent groups in R2 and R3 described in the above may further have a substituent group. The substituent group which may be further possessed is not particularly limited, and alkyl, alkenyl, phenyl, hydroxy, alkoxy, phenoxy, amino, alkylthio, phenylthio, halogen atom, hetero ring residue and the like can be exemplified, though not always limited thereto.

R2 is preferably hydrogen atom, an alkyl group having from 1 to 8 carbon atoms, an alkoxyl group having from 1 to 8 carbon atoms, cyano group or a halogen atom, more preferably hydrogen atom, an alkyl group having from 1 to 4 carbon atoms, cyano group, chlorine atom or fluorine atom, further preferably hydrogen atom or methyl group.

R3 is preferably hydrogen atom, an alkyl group having from 1 to 8 carbon atoms, an alkoxyl group having from 1 to 8 carbon atoms, cyano group or a halogen atom, more preferably hydrogen atom, an alkyl group having from 1 to 4 carbon atoms, an alkoxyl group having from 1 to 4 carbon atoms, cyano group, chlorine atom or fluorine atom, further preferably hydrogen atom, an alkyl group having from 1 to 4 carbon atoms, chlorine atom or fluorine atom.

In formula (III), Y represents a hydrogen atom or an oxygen atom, and preferably represents a hydrogen.

The compound (I) of the invention has two asymmetric centers in the molecule and is present as a pair of diastereomers. Each diastereomer is further composed of a pair of enantiomers. Thus, though four optical isomers are present, all of the isolated forms of diastereomers and enantiomers and mixtures thereof are included in the invention. According to the invention, preferred is a structure represented by the following formula (I'). In the formula, R1 has the same meaning as R1 in the above formula (I).

(I')

The compound of the invention may be in the form of a pharmaceutically acceptable salt. According to the invention, the pharmaceutically acceptable salt means a salt which is safe and nontoxic, is innocuous not only biologically but also other than that and has the desirable pharmacological activity of its parent compound. Such a salt is derived from an inorganic or organic acid or base. Its illustrative examples include an acid addition salt with hydrochloric acid, hydrobromic acid, hydriodic acid, sulfuric acid, nitric acid, phosphoric acid or the like inorganic acid; an acid addition salt with formic acid, acetic acid, propionic acid, oxalic acid, inalonic acid, succinic acid, fumaric acid, maleic acid, lactic acid, malic acid, tartaric acid, citric acid, methanesulfonic acid, ethanesulfonic acid, aspartic acid, glutamic acid, p-toluenesulfonic acid, trimethylacetic acid, 2,2,2-trifluoroacetic acid or the like organic acid; a salt which is formed through the substitution by a metal ion such as sodium, potassium, magnesium, calcium, aluminum or the like alkali metal ion or alkaline earth metal ion; ammonium salt; a salt with methylamine, ethylamine, ethanolamine, diethanolamine, triethanolamine or the like organic base, and the like. Further according to the invention, inner salts and addition products, various hydrates and solvates and polymorphic substances are also included in the compound of the invention and addition salts thereof.

In addition, all of the compounds which are converted to the compound of the invention and salts thereof in the living body, so-called prodrugs, are also included in the compound of the invention.

Illustrative examples of the compound of the invention are cited in the following, but the invention is not limited thereto.

I-1

I-2

Next, production method of the compounds of the invention is described.

It is possible to synthesize the compound of the invention and pharmaceutically acceptable salts thereof by combining various conventionally known reactions in response to their basic skeletons and kinds of substituent groups. As the synthesizing method of the compounds of the invention, examples of a case in which R1 in the aforementioned formula (I) is the structure of the aforementioned formula (II) and a case in which it is the structure of the aforementioned formula (III) are respectively shown, though the invention is not limited thereto.

Scheme 1

----- represents single bond or double bond

In the formulae, *, R2 and R3 represents the same meanings as described in the foregoing.

The compounds of interest of the invention, (IA), (IA') and (IA"), can be synthesized by heating an epoxy compound (IB) and a pyridylpyridone derivative (IIa) or reduced form of bipyridine (IIIa) in an appropriate solvent in the presence of a catalyst.

Firstly, the reaction of epoxy compound (IB) with pyridylpyridone derivative (IIa) in the above-mentioned Scheme 1 is described.

The epoxy compound (IB) as a starting material is broadly known as an intermediate of conventionally known azole system antifungal agents and can be synthesized by a generally used method (e.g., JP-A-191262 or the like).

Another starting material, pyridylpyridone derivative (IIa), can be easily synthesized by preparing its precursor bipyridine compound (IIb) by conventionally known methods (Japanese Patent No. 3,032,980, Japanese Patent No. 3,272,326, JP-A-2001-158773 and the like) and hydrolyzing the bipyridine compound (IIb) with a strong acid ("Jikken kagaku Koza (Experimental Chemistry Course)" 4th edition, vol. 21, pp. 181-182, 1991, and the like).

Scheme 2

In the reaction of epoxy compound (IB) with pyridylpyridone derivative (IIa), amount of the pyridylpyridone derivative to be used is generally from 1 to 20 moles, preferably from 1 to 5 moles, more preferably from 1 to 3 moles, based on 1 mole of the epoxy compound.

Examples of the base to be used in the reaction of epoxy compound (IB) with pyridylpyridone derivative (IIa) include metallic sodium, sodium hydride, lithium hydride, sodium carbonate, potassium carbonate, cesium carbonate, calcium oxide, lithium hydroxide, potassium phosphate and the like inorganic bases; pyridine, 2-methylpyridine, diethylamine, diisopropylamine, triethylamine, phenylethylamine, isopropylethylamine, methylaniline, tetrabutylammonium hydroxide, 1,8-diazabicyclo[5,4,0]undec-7-ene, potassium acetate and the like organic bases; and potassium tert-butoxide, sodium tert-butoxide, sodium methoxide, sodium ethoxide and the like metal alkoxides. Preferred among them are inorganic bases and more preferred are sodium hydride, lithium hydride and cesium carbonate. In addition, two or more bases can be jointly used in the invention, and using ratio of respective bases in the case of mixed use can be optionally set. Amount of the base to be used varies depending on the substrate but is generally from 0.1 to 20 moles, preferably from 0.5 to 10 moles, more preferably from 1 to 5 moles, based on 1 mole of the epoxy compound.

The solvent to be used in the reaction of epoxy compound (IB) with pyridylpyridone derivative (IIa) is not particularly limited with the proviso that it does not take part in the reaction, and for example, any one of benzene, toluene, xylene, chlorobenzene, dichlorobenzene and the like aromatic solvents; pyridine, acetonitrile, N,N-dimethylformamide, N,N-dimethylacetamide, N-methylpyrrolidone and the like polar solvents; diethyl ether, diisopropyl ether, dibutyl ether, methyl t-butyl ether, tetrahydrofuran and the like ether system solvents, and the like can be used regardless of polar or non-polar solvent. Preferred are diisopropyl ether, dibutyl ether, methyl t-butyl ether, tetrahydrofuran and the like ether system solvents and acetonitrile, N,N-dimethylformamide, N,N-dimethylacetamide, N-methylpyrrolidone and the like polar solvents, and more preferred are acetonitrile, N,N-dimethylformamide and N,N-dimethylacetamide. In addition, two or more solvents can be used by mixing them, and their mixing ratio in the case of mixed use can be optionally set. Amount of the above-mentioned reaction solvent to be used is within the range of from 1 to 50 times in weight, preferably from 2 to 30 times in weight, more preferably from 5 to 20 times in weight, based on the bipyridine derivative.

The reaction temperature of this step is generally within the range of from 0 to 200° C., preferably from 10 to 120° C., more preferably from 20 to 100° C. The reaction time of this step is generally from 10 minutes to 24 hours, and the reaction is completed within 15 hours in most cases.

Since the compounds of interest (IA) and (IA') are obtained as a mixture by the reaction of epoxy compound (IB) with pyridylpyridone derivative (IIa), column purification is carried out using silica gel. In addition, a usual organic compound isolation purification method may be used after the column purification. For example, purification is carried out by recrystallization using ethyl acetate, toluene, an alcohol, hexane or the like, distillation under a reduced pressure, and the like. When the purification is carried out by these methods alone or in combination of two or more, it is possible to obtain the specified substance with a high purity.

In addition, it is possible to separate diastereomers by a fractional recrystallization, column chromatography or the like generally used method, and enantiomers using a commercially available optical isomer separation column or the like, respectively.

Next, the reaction of epoxy compound (IB) with bipyridine reductant (IIIa) of the above-mentioned Scheme 2 is described.

The starting substance bipyridine reductant (IIIa) can be easily prepared by using a commercially available bipyridine derivative, or synthesizing a bipyridine derivative by a conventionally known method (e.g., Japanese Patent No. 3,032, 980, Japanese Patent No. 3,272,326, JP-A-2001-158773, JP-A-2005-213239 or the like), and then carrying out a reducing reaction (e.g., Wo 2005/16910; Bull. Soc. Chim, Fr., 1996, pp. 369-380, or the like).

In the reaction of epoxy compound (IB) with bipyridine reductant (IIIa), amount of the bipyridine reductant to be used is generally from 0.8 to 20 moles, preferably from 1 to 15 moles, more preferably from 2 to 10 moles, based on 1 mole of the epoxy compound.

As the catalyst to be used in the reaction of epoxy compound (IB) with bipyridine reductant (IIIa), it is desirable to use an inorganic salt. Its illustrative examples include lithium chloride, lithium perchlorate, lithium bromide, lithium chlorite, lithium sulfate, lithium carbonate, lithium phosphate and the like lithium salts; sodium chloride, sodium phosphate, sodium chlorate, sodium perchlorate and the like sodium salts; potassium perchlorate and the like potassium salts; and cesium chloride, cesium carbonate and the like cesium salts. Preferred is a lithium salt and more preferred is lithium perchlorate. Amount of the catalyst to be used is generally from 0.1 to 20 moles, preferably from 0.5 to 15 moles, more preferably from 1 to 10 moles, based on 1 mole of the epoxy compound.

The solvent to be used in the reaction of epoxy compound (IB) with bipyridine reductant (IIIa) is not particularly limited with the proviso that it does not take part in the reaction, and for example, anyone of benzene, toluene, xylene, chlorobenzene, dichlorobenzene and the like aromatic solvents; acetonitrile, N,N-dimethylformamide, N,N-dimethylacetamide, N-methylpyrrolidone and the like polar solvents; diethyl ether, diisopropyl ether, dibutyl ether, methyl t-butyl ether, tetrahydrofuran and the like ether system solvents, and the like can be used regardless of polar or non-polar solvent. Preferred are diisopropyl ether, dibutyl ether, methyl t-butyl ether, tetrahydrofuran and the like ether system solvents and acetonitrile, N,N-dimethylformamide, N,N-dimethylacetamide, N-methylpyrrolidone and the like polar solvents, and more preferred are acetonitrile, N,N-dimethylformamide and N,N-dimethylacetamide. In addition, two or more solvents can be used by mixing them, and their mixing ratio in the case of mixed use can be optionally set. Amount of the above-mentioned reaction solvent to be used is within the range of from 1 to 50 times in weight, preferably from 2 to 30 times in weight, more preferably from 5 to 20 times in weight, based on the bipyridine derivative.

The reaction temperature in the reaction of epoxy compound (IB) with bipyridine reductant (IIIa) is generally within the range of from 0 to 200° C., preferably from 10 to 180° C., more preferably from 20 to 120° C. In addition, the reaction time of this reaction is generally from 10 minutes to 60 hours, and the reaction is completed within 48 hours in most cases.

After completion of the reaction, the thus obtained compound of interest (IA") can be subjected to a usual organic compound isolation purification method. For example, purification is carried out by recrystallization using ethyl acetate, toluene, an alcohol, hexane or the like, distillation under a reduced pressure, and the like. When the purification is carried out by these methods alone or in combination of two or more, it is possible to obtain the specified substance with a high purity.

In addition, it is possible to separate diastereomers by a fractional recrystallization, column chromatography or the like generally used method, and enantiomers using a commercially available optical isomer separation column or the like, respectively.

EXAMPLES

The following describes the invention further illustratively based on examples, but the invention is not limited thereto.

Example 1

Synthesis of (2R,3R)-2-(2,4-difluorophenyl)-3-(4-pyridin-2-ylpiperidin-1-yl)-1-(1,2,4-triazol-1-yl)butan-2-ol (I-1)

(2R,3R)-2-(2,4-Difluorophenyl-3-methyl-2-(1H-1,2,4-triazol-1-ylmethyl)oxirane (0.76 g, 3.0 mmol) and 2-(4-piperidyl)pyridine (4.3 g, 26.5 mmol) were dissolved in acetonitrile (50 ml), and lithium perchlorate trihydrate (4.25 g, 26.5 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.37 g of the intended substance (yield 28.9%).

Example 2

Synthesis of (2R,3R)-2-(2,4-difluorophenyl)-3-[4-(5-fluoropyridin-2-yl) piperidin-1-yl]-1-(1,2,4-triazol-1-yl)butan-2-ol (I-2)

(2R,3S)-2-(2,4-Difluorophenyl)-3-methyl-2-(1H-1,2,4-triazol-1-ylmethyl)oxirane (0.76 g, 3.0 mmol) and 5-fluoro-2-piperidin-4-ylpyridine (4.7 g, 26.5 mmol) were dissolved in acetonitrile (50 ml), and lithium perchlorate trihydrate (4.25 g, 26.5 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.45 g of the intended substance (yield 34.8%).

Example 3

Synthesis of (2R,3R)-2-(2,4-difluorophenyl)-3-(3',6'-dihydro-2,4'-bipyridin-1'(2'H)-yl)-1-(1,2,4-triazol-1-yl)butan-2-ol (I-3)

(2R,3S)-2-(2,4-Difluorophenyl)-3-methyl-2-(1H-1,2,4-triazol-1-ylmethyl)oxirane (2.21 g, 8.8 mmol) and 1',2',3',6'-tetrahydro-2,4'-bipyridine (7.47 g, 46.6 mmol) were dissolved in acetonitrile (100 ml), and lithium perchlorate trihydrate (7.48 g, 46.6 mmol) was added thereto and refluxed for 48 hours. The solvent was evaporated under a reduced pressure, and the thus obtained residue was dissolved in ethyl acetate and washed with water. The solvent was again evaporated under a reduced pressure, and the residue was purified using a silica gel column to obtain 1.90 g of the intended substance (yield 49.6%).

Example 4

Synthesis of (2R,3R)-2-(2,4-difluorophenyl)-3-(5,6-dimethyl-3',6'-dihydro-2,4'-bipyridin-1'(2'H)-yl)-1-(1,2,4-triazol-1-yl)butan-2-ol (I-4)

(2R,3S)-2-(2,4-Difluorophenyl)-3-methyl-2-(1H-1,2,4-triazol-1-ylmethyl)oxirane (0.83 g, 3.3 mmol) and 5,6-dimethyl-1',2',3',6'-tetrahydro-2,4'-bipyridine (5.18 g, 27.5 mmol) were dissolved in acetonitrile (50 ml), and lithium perchlorate trihydrate (7.48 g, 46.6 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.67 g of the intended substance (yield 44.7%).

Example 5

Synthesis of (2R,3R)-2-(2,4-difluorophenyl)-3-(5-methyl-3',6'-dihydro-2,4'-bipyridin-1'(2'H)-yl)-1-(1,2,4-triazol-1-yl)butan-2-ol (I-5)

(2R,3S)-2-(2,4Difluorophenyl)-3-methyl-2-(1H-1,2,4-triazol-1-ylmethyl)oxirane (0.76 g, 3.0 mmol) and 5-methyl-1',2',3',6'-tetrahydro-2,4'-bipyridine (1.63 g, 9.3 mmol) were dissolved in acetonitrile (20 ml), and lithium perchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.63 g of the intended substance (yield 47.8%).

Example 6

Synthesis of (2R,3R)-3-(5-chloro-3',6'-dihydro-2,4'-bipyridin-1'(2'H)-yl)-2-(2,4-difluorophenyl)-1-(1,2,4-triazol-1-yl)butan-2-ol (I-6)

(2R,3S)-2-(2,4-Difluorophenyl)-3-methyl-2-(1H-1,2,4-triazol-1-ylmethyl)oxirane (0.76 g, 3.0 mmol) and 5-chloro-1',2',3',6'-tetrahydro-2,4'-bipyridine (1.31 g, 6.7 mmol) were dissolved in acetonitrile (20 ml), and lithium perchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.88 g of the intended substance (yield 63.8%).

Example 7

Synthesis of (2R,3R)-2-(2,4-difluorophenyl)-3-(5-fluoro-3',6'-dihydro-2,4'-bipyridin-1'(2'H)-yl)-1-(1,2,4-triazol-1-yl)butan-2-ol (I-7)

(2R,3S)-2-(2,4-Difluorophenyl)-3-methyl-2-(1H-1,2,4-triazol-1-ylmethyl)oxirane (0.76 g, 3.0 mmol) and 5-fluoro-1',2',3',6'-tetrahydro-2,4'-bipyridine (1.63 g, 9.3 mmol) were dissolved in acetonitrile (20 ml), and lithium perchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.63 g of the intended substance (yield 47.8%).

Examples 8 and 9

Synthesis of 1'-[(1R,2R)-2-(2,4-difluorophenyl)-2-hydroxy-1-methyl-3-(1,2,4-triazol-1-yl)propyl]-2,4'-bipyridin-2'-one (I-8) and (2R,3R)-3-(2,4'-bipyridin-2'-yloxy)-2-(2,4-difluorophenyl)-1-(1,2,4-triazol-1-yl)butan-2-ol (I-9)

(2R,3S)-2-(2,4-Difluorophenyl)-3-methyl-2-(1H-1,2,4-triazol-1-ylmethyl)oxirane (3.7 g, 14.7 mmol) and 2,4'-bipyridin-2'-one (4.4 g, 25.6 mmol) were dissolved in dimethylformamide (50 ml), and cesium carbonate (10.3 g, 31.7 mmol) and sodium hydride (8.1 g, 28.2 mmol) were added thereto and allowed to undergo the reaction at 60° C. for 10 hours. This was mixed with water (150 ml) and extracted with dichloromethane (70 ml). The extraction operation was repeated three times, and the obtained organic layer was evaporated. By purifying the residue using a silica gel column, 2.26 g of an oily form of the intended substance (I-8) (yield 37.0%) and 0.58 g of the intended substance (I-9) (yield 9.2%) were respectively obtained.

Example 10

Synthesis of (2R,3R)-2-(2,4-difluorophenyl)-3-(5',6'-dihydro-2,3'-bipyridin-1'(2'H)-yl)-1-(1,2,4-triazol-1-yl)butan-2-ol (I-10)

(2R,3S)-2-(2,4-Difluorophenyl)-3-methyl-2-(1H-1,2,4-triazol-1-ylmethyl)oxirane (0.83 g, 3.3 mmol) and 1',2',5',6'-tetrahydro-2,3'-bipyridine (3.51 g, 21.9 mmol) were dissolved in acetonitrile (50 ml), and lithiumperchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.87 g of the intended substance (yield 61.9%).

Example 11

Synthesis of (2R,3R)-2-(2,4-difluorophenyl)-3-(5,6-dimethyl-5',6'-dihydro-2,3'-bipyridin-1'(2'H)-yl)-1-(1,2,4-triazol-1-yl)butan-2-ol (I-11)

(2R,3S)-2-(2,4-Difluorophenyl)-3-methyl-2-(1H-1,2,4-triazol-1-ylmethyl)oxirane (0.76 g, 3.0 mmol) and 5,6-dimethyl-1',2',5',6'-tetrahydro-2,3'-bipyridine (3.96 g, 21.0 mmol) were dissolved in acetonitrile (50 ml), and lithium perchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.35 g of the intended substance (yield 35.7%).

Example 12

Synthesis of (2R,3R)-2-(2,4-difluorophenyl)-3-(3-pyridin-2-ylpiperidin-1-yl)-1-(1,2,4-triazol-1-yl)butan-2-ol (I-12)

(2R,3S)-2-(2,4-Difluorophenyl)-3-methyl-2-(1H-1,2,4-triazol-1-ylmethyl)oxirane (0.87 g, 3.5 mmol) and 2-piperidin-3-ylpyridine (2.80 g, 17.26 mmol) were dissolved in acetonitrile (50 ml), and lithium perchlorate trihydrate (1.50 g, 9.3 mmol) was added thereto and refluxed for 40 hours. The solvent was evaporated under a reduced pressure, and the thus obtained residue was dissolved in ethyl acetate and washed with water. The solvent was again evaporated under a reduced pressure, and the residue was purified using a silica gel column to obtain 0.35 g of the intended substance (yield 35.7%).

Results of the measurement of melting point and NMR of Examples 1 to 12 are shown in Table 1.

TABLE 1

| No. | Melting point (° C.) | $^{1}$H-NMR, 400 MHz |
|---|---|---|
| 1 | 74-77 | Solvent: DMSO<br>δ: 8.49 (d, J = 4.0 Hz, 1H), 8.32 (s, 1H), 7.68-7.32 (m, 2H), 7.35 (dd, J = 7.2 Hz, 1H), 7.29 (d, J = 7.6 Hz, 1H), 7.19 (dd, J = 7.2, 5.6 Hz, 1H), 7.11 (dd, 1H), 6.91 (dd, 1H), 5.5 (br, 1H), 4.85 (d, J = 23.3 Hz, 1H), 4.83 (d, J = 22.8 Hz, 1H), 3.20 (d, J = 10.8 Hz, 1H), 3.13 (m, 2H), 2.65 (m, 1H), 2.62 (m, 2H), 2.25 (dd, 1H), 1.87 (m, 2H), 0.81 (d, J = 6.8 Hz, 3H) |
| 2 | 100-102 | Solvent: DMSO<br>δ: 8.47 (d, J = 2.8 Hz, 1H), 8.32 (s, 1H), 7.68 (s, 1H), 7.64 (dt, J = 3.2, 8.8 Hz, 1H), 7.37 (m, 2H), 7.12 (m, 1H), 6.93 (dt, J = 2.4, 8.4 Hz, 1H), 5.52 (s, 1H), 4.84 (d, J = 24.0 Hz, 1H), 4.83 (d, J = 24.4 Hz, 1H), 3.20 (d, J = 11.2 Hz, 1H), 3.13 (q, J = 6.8 Hz, 1H), 2.80 (m, 1H), 2.65 (m, 2H), 2.25 (t, J = 8.8 Hz, 1H), 1.90-1.76 (m, 3H) 0.81 (d, J = 6.8 Hz, 3H) |
| 3 | 123.5-126.5 | Solvent: CDCl$_3$<br>δ: 8.57 (d, J = 2.8 Hz, 1H), 8.01 (s, 1H), 7.78 (s, 1H), 7.66 (s, 1H), 7.53 (q, J = 6.8 Hz, 1H), 7.39 (d, J = 7.7 Hz, 1H), 7.16 (t, J = 6.0 Hz, 1H), 6.76 (m, 2H), 6.65 (s, 1H), 5.39 (s, 1H), 4.92 (m, 2H), 3.48 (m, 1H), 3.27 (s, 1H), 3.05-2.99 (m, 2H), 2.60 (m, 3H), 1.05 (d, J = 3.2 Hz, 3H) |
| 4 | 85.5-87.5 | Solvent: DMSO<br>δ: 8.28 (s, 1H), 7.65 (s, 1H), 7.46 (d, J = 8.0 Hz, 1H), 7.33 (dd, J = 16.0, 8.8 Hz, 1H), 7.23 (d, J = 8.0 Hz, 1H), 7.12 (dd, J = 9.6, 9.6 Hz, 1H), 6.92 (dd, J = 8.8, 8.8 Hz, 1H), 6.64 (s, 1H), 5.52 (s, 1H), 4.81 (m, 2H), 3.52-3.32 (m, 4H), 2.57 (m, 3H), 2.41 (s, 3H), 2.23 (s, 3H), 0.82 (d, J = 6.8 Hz, 3H) |
| 5 | 115-117 | Solvent: DMSO<br>δ: 8.37 (d, J = 2.0 Hz, 1H), 8.29 (s, 1H), 7.66 (s, 1H), 7.57 (dd, J = 8.4, 2.0 Hz, 1H), 7.44 (d, J = 8.0 Hz, 1H), 7.34 (dq, J = 2.0, 8.8 Hz, 1H), 7.13 (dt, J = 2.8, 9.2 Hz, 1H), 6.93 (dt, J = 8.4, 2.4 Hz, 1H), 6.67 (s, 1H), 5.52 (s, 1H), 4.82 (m, 2H), 3.51 (dd, J = 2.4, 17.6 Hz, 1H), 3.3-3.15 (m, 3H), 2.6-2.5 (m, 3H), 2.28 (s, 3H), 0.82 (d, J = 6.8 Hz, 3H) |
| 6 | 158-159 | Solvent: DMSO<br>δ: 8.56 (d, J = 2.4 Hz, 1H), 8.29 (s, 1H), 7.88 (dd, J = 2.4, 8.4 Hz, 1H), 7.66 (s, 1H), 7.60 (d, J = 8.4 Hz, 1H), 7.33 (q, J = 8.8 Hz, 1H), 7.14 (dt, J = 2.4, 8.8 Hz, 1H), 6.92 (dt, J = 2.4, 8.8 Hz, 1H), 6.78 (s, 1H), 5.54 (s, 1H), 4.82 (m, 2H), 3.53 (dd, J = 18.0, 2.4 Hz, 1H), 3.38-3.16 (m, 3H), 2.61-2.50 (m, 3H), 0.82 (d, J = 6.8 Hz, 3H) |
| 7 | 148-150 | Solvent: DMSO<br>δ: 8.52 (d, J = 3.2 Hz, 1H), 8.29 (s, 1H), 7.66 (m, 3H), 7.34 (q, J = 6.8 Hz, 1H), 7.12 (dt, J = 2.4, 9.2 Hz, 1H), 6.93 (dt, J = 2.4, 8.4 Hz, 1H), 6.8 (s, 1H), 5.54 (s, 1H), 4.84 (d, J = 19.2 Hz, 1H), 4.81 (d, J = 18.8 Hz, 1H), 3.52 (d, J = 16.0 Hz, 1H), 3.36-3.16 (m, 3H), 2.61-2.50 (m, 3H), 0.82 (d, J = 6.8 Hz, 3H) |
| 8 | — | Solvent: CDCl$_3$<br>δ: 8.75 (d, J = 4.8 Hz, 1H), 8.28 (d, J = 4.8 Hz, 1H), 7.95 (s, 1H), 7.83 (ddd, J = 8.0, 8.0, 1.6 Hz, 1H), 7.77-7.45 (m, 2H), 7.57-7.51 (m, 2H), 7.44 (s, 1H), 7.36 (ddd, J = 8.0, 6.0, 1.2 Hz, 1H), 6.79-6.76 (m, 2H), 5.89 (q, J = 6.4 Hz, 1H), 5.00 (d, J = 14.4 Hz, 1H), 4.73 (d, J = 14.4 Hz, 1H), 1.21 (d, J = 6.4 Hz, 3H) |
| 9 | 178-180 | Solvent: CDCl$_3$<br>δ: 8.76 d, J = 4.4 Hz, 1H), 7.92 (d, J = 7.2 Hz, |

TABLE 1-continued

| No. | Melting point (° C.) | $^1$H-NMR, 400 MHz |
|---|---|---|
|  |  | 1H), 7.86 (dd, J = 7.2, 7.2 Hz, 1H), 7.81 (m, 1H), 7.73 (s, 1H), 7.48 (m, 1H), 7.40 (m, 1H), 7.15 (d, J = 2.0 Hz, 1H), 7.05 (d, J = 8.0 Hz, 1H), 6.80 (m, 2H), 6.01 (q, J = 7.2 Hz, 1H), 5.37 (s, 1H), 5.25 (d, J = 13.2 Hz, 1H), 4.04 (d, J = 13.2 Hz, 1H), 1.23 (d, J = 7.2 Hz, 3H) |
| 10 | 89-92 | Solvent: DMSO δ: 8.51 (d, J = 2.4 Hz, 1H), 8.27 (s, 1H), 7.74 (dd, J = 7.6, 1.6 Hz, 1H), 7.66 (s, 1H), 7.58 (d, J = 8.0 Hz, 1H), 7.34 (m, 1H), 7.23 (dd, J = 7.2, 4.2 Hz, 1H), 7.13 (t, J = 9.2 Hz, 1H), 6.91 (t, J = 8.4 Hz, 1H), 6.73 (s, 1H), 5.54 (s, 1H), 4.83 (s, 2H), 3.67 (m, 2H), 3.30 (m, 1H), 3.10 (m, 1H), 2.5-2.30 (m, 3H), 0.83 (d, J = 6.8 Hz, 3H) |
| 11 | — | Solvent: DMSO δ: 8.28 (s, 1H), 7.66 (s, 1H), 7.45 (d, J = 8.4 Hz, 1H), 7.35 (dd, J = 7.2 Hz, 1H), 7.26 (d, J = 8.0 Hz, 1H), 7.13 (dd, J = 5.6 Hz, 1H), 6.92 (dd, 1H), 6.64 (s, 1H), 5.55 (s, 1H), 4.82 (s, 2H), 3.63 (m, 2H), 3.30 (m, 1H), 3.10 (m, 1H), 2.5-2.2 (m, 3H), 2.40 (s, 3H), 2.22 (s, 1H), 0.87 (d, J = 6.8 Hz, 3H) |
| 12 | 75-78 | Solvent: DMSO δ: 8.49 (d, J = 4.8 Hz, 1H), 8.30 (s, 1H), 7.69 (m, 2H), 7.31 (m, 2H), 7.21 (m, 1H), 7.10 (m, 1H), 6.90 (m, 1H), 5.56 (s, 1H), 4.83 (m, 2H), 3.28 (m, 1H), 3.12 (m, 1H), 3.00 (m, 1H), 2.70 (m, 1H), 2.50 (m, 1H), 2.34 (m, 1H), 1.90 (m, 1H), 1.7 (m, 2H), 1.50 ((m, 1H), 0.79 (d, J = 6.8 Hz, 3H) |

Test Example 1

Antifungal Activity Test (In Vitro)

Minimum inhibitory concentration (MIC) of each of the compounds obtained in Examples 1 to 12 was measured for respective fungi at MOS Pharm Service, by the methods described in Antimicrobial Agents and Chemotherapy, vol. 3, pp. 40-48 (1973), Antimicrobial Agents and Chemotherapy, vol. 33, pp. 215-222 (1989) and Antimicrobial Agents and Chemotherapy, vol. 38, pp. 2362-2368 (1994). The measuring conditions are shown in the following. In this case, Voriconazol was used as a comparative compound.

*Candida albicans* ATCC 10231 and ATCC 44858; Cultured at 37° C. for 20 hours using fluid Sabouraud medium, and this was used as a cell suspension.

*Aspergillus fumigatus* ATCC 1028; Cultured at 28° C. for 2 days using potato dextrose broth, and this was used as a cell suspension.

*Cryptococcus neoformans* ATCC 24067, *Pityrosporum ovale* ATCC 38593; Cultured at 37° C. for 2 day using fluid Sabouraud medium, and this was used as a cell suspension.

*Microsporum canis* ATCC 36299; Cultured at 30° C. for 2 days using fluid Sabouraud medium, and this was used as a cell suspension.

*Trichophyton mentagrophytes* ATCC 9533; Cultured at 28° C. for 3 days using fluid Sabouraud medium, and this was used as a cell suspension.

*Trichophyton rubrum* ATCC 10218; Cultured at 28° C. for 3 days using fluid Sabouraud medium, and this was used as a cell suspension.

*Aspergillus niger* ATCC 8740; Cultured at 28° C. for 2 days using potato dextrose broth, and this was used as a cell suspension.

Each of the compounds of the invention was adjusted to a concentration of 1% by weight using dimethyl sulfoxide (DMSO) and a medium similar to the respective medium used in the above-mentioned fungal culture, having a final concentration of from 0.001 to 100 μg/ml, was prepared. Each of the inoculation cell suspensions prepared by the above-mentioned methods was inoculated onto this agar plate. The medium was subjected to a static culturing at 28 to 37° C. for 1 to 3 days, and the minimum drug concentration which distinctively inhibited growth of hyphae in comparison with the drug-free control was used as the MIC value. The results are shown in Table 2. In this connection, Voriconazol was used as the comparative compound C-1.

TABLE 2

| Fungal species | MIC value (μg/ml) | | | | | | | | | | | | |
|---|---|---|---|---|---|---|---|---|---|---|---|---|---|
|  | I-1 | I-2 | I-3 | I-4 | I-5 | I-6 | I-7 | I-8 | I-9 | I-10 | I-11 | I-12 | C-1 |
| *Candida albicans* (ATCC 10231) | 0.3 | 0.1 | 0.3 | 0.3 | 0.1 | 0.01 | 0.1 | 0.1 | 0.3 | 3 | 100 | 0.1 | 0.3 |
| *Aspergillus fumigatus* (ATCC 1028) | 10 | 10 | 1 | 10 | 3 | 1 | 10 | 100 | 30 | 100 | 100 | 100 | 0.3 |
| *Cryptococcus neoformans* (ATCC 24067) | 0.1 | 0.3 | 0.3 | 0.1 | 0.03 | 0.03 | 0.3 | 0.3 | 0.3 | 1 | 0.3 | 10 | 0.1 |
| *Microsporum canis* (ATCC 36299) | 0.3 | 10 | 0.03 | 1 | 1 | 0.3 | 10 | 10 | 10 | 100 | 10 | 100 | 3 |
| *Trichophyton mentagrophytes* (ATCC 9533) | 0.3 | 1 | 0.1 | 0.3 | 0.1 | 0.1 | 1 | 30 | 10 | 3 | 10 | 100 | 0.1 |
| *Pityrosporum ovale* (ATCC 38593) | 0.3 | 0.01 | 0.003 | 10 | 0.003 | 0.003 | 0.01 | 1 | 0.3 | 0.3 | 0.1 | 10 | 0.3 |
| *Candida albicans* (ATCC 44858) | — | — | 1 | — | — | — | — | — | — | — | — | — | 0.3 |
| *Trichophyton rubrum* (ATCC 10218) | — | — | 0.3 | — | — | — | — | — | — | — | — | — | 0.3 |

TABLE 2-continued

| Fungal species | MIC value (µg/ml) | | | | | | | | | | | | |
|---|---|---|---|---|---|---|---|---|---|---|---|---|---|
| | I-1 | I-2 | I-3 | I-4 | I-5 | I-6 | I-7 | I-8 | I-9 | I-10 | I-11 | I-12 | C-1 |
| Aspergillus niger (ATCC 8740) | — | — | 1 | — | — | — | — | — | — | — | — | — | 0.1 |

It is evident from the above-mentioned results that the compounds of the invention have excellent antifungal action and are particularly effective for *Candida, Cryptococcus* and *Pityrosporum*. The compounds of the invention are useful as superior antifungal therapeutic agents.

Test Example 2

Antifungal Activity Test (In Vivo)

With respect to compounds I-1, I-3 and I-6 obtained in Examples 1, 3 and 6 respectively, therapeutic effects at the time of subcutaneous administration of compounds I-1, I-3 and I-6 on a mouse systemic infection model by *Candida albicans* TIMM 1623 were tested.

The test was carried out using 5 animals for each of the drug administration groups and Negative control group (sterile physiological saline administration group).

Each of compounds I-1, I-3 and I-6 was dissolved in and diluted with dimethyl sulfoxide (DMSO; Wako Pure Chemical Industries, Ltd.) and then prepared into a predetermined concentration by diluting with sterile physiological saline.

As the control experiment, Fluconazole (FLCZ, Flanos intravenous drip solution 100 mg; TOYAMA CHEMICAL CO, LTD.) diluted to a predetermined concentration with sterile physiological saline was used.

On the next day of the receipt of animals, body weights of mice were measured and CP (crude protein) was intraperitoneally administered at a dose of 200 mg/kg based on the individual body weight, and then they were reared for 3 days.

Cells of *C. albicans* TIMM 1623 cultured overnight at 35° C. on SDA (Sabouraud dextrose agar; Eiken Chemical Co., Ltd.) plate medium were suspended in sterile physiological saline and used as the Stock solution, and a portion thereof was diluted with 10% formalin (Wako Pure Chemical Industries, Ltd.). The number of cells in the diluted liquid was counted under a biological microscope using a hemocytometer, and then an inoculum was prepared by diluting the stock solution with sterile physiological saline (about $1.5 \times 10^5$ cells/ml). By inoculating 0.2 ml of this cell suspension through caudal vein, infection was induced. In this connection, the number of viable cells in the inoculum was verified by spreading the cell suspension optionally diluted with sterile physiological saline on an SDA plate medium and then culturing at 35° C. Each of the substances to be tested, control substance or sterile physiological saline was subcutaneously administered after 2 hours of the infection and for 3 days starting on the next day of infection once a day, a total of 4 times. After measuring individual body weight on the next day of infection, CP was again administered intraperitoneally at a dose of 100 mg/kg. The number of survived mice was observed and recorded for 14 days starting on the next day of infection.

Figure 1A:
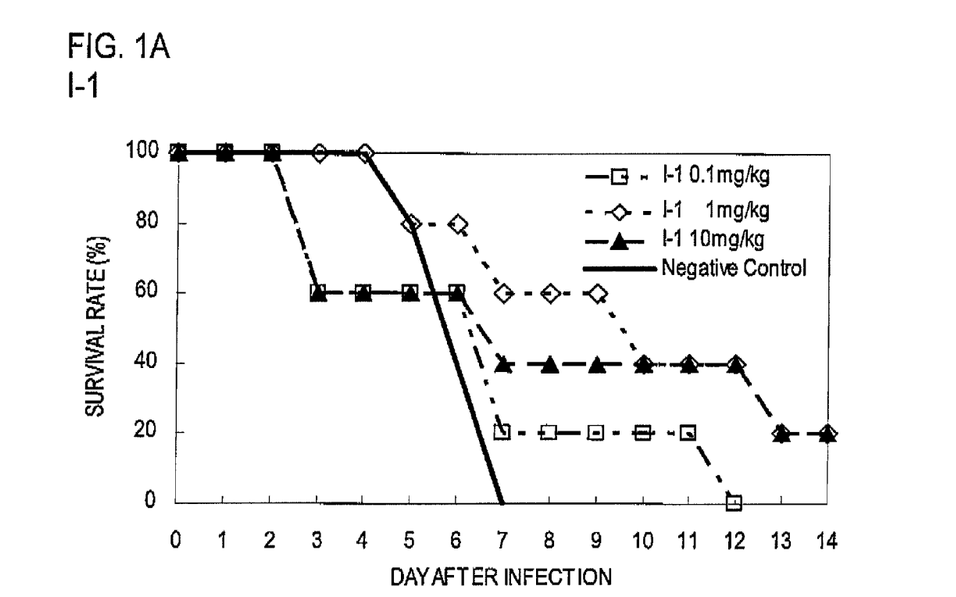
Figure 1B:
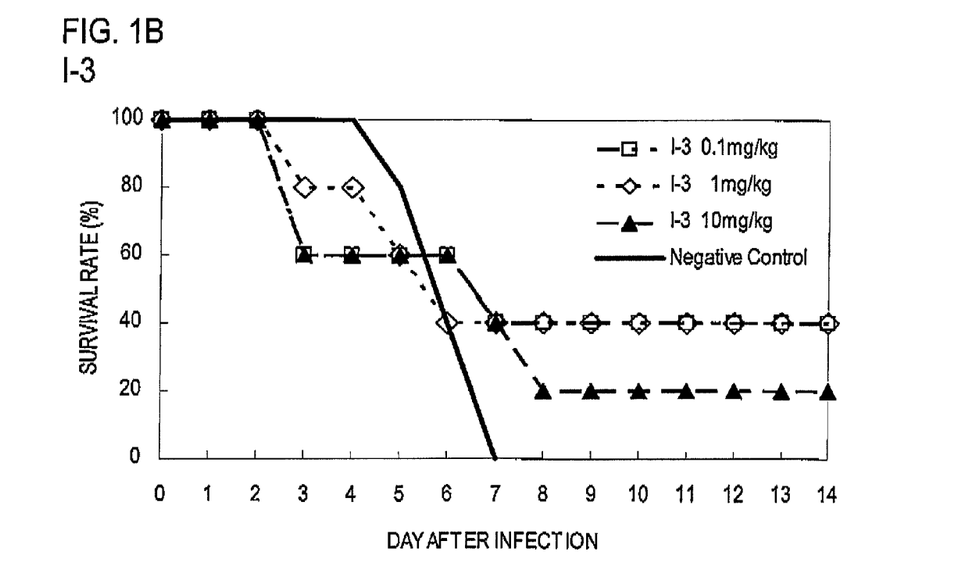
Figure 1C:
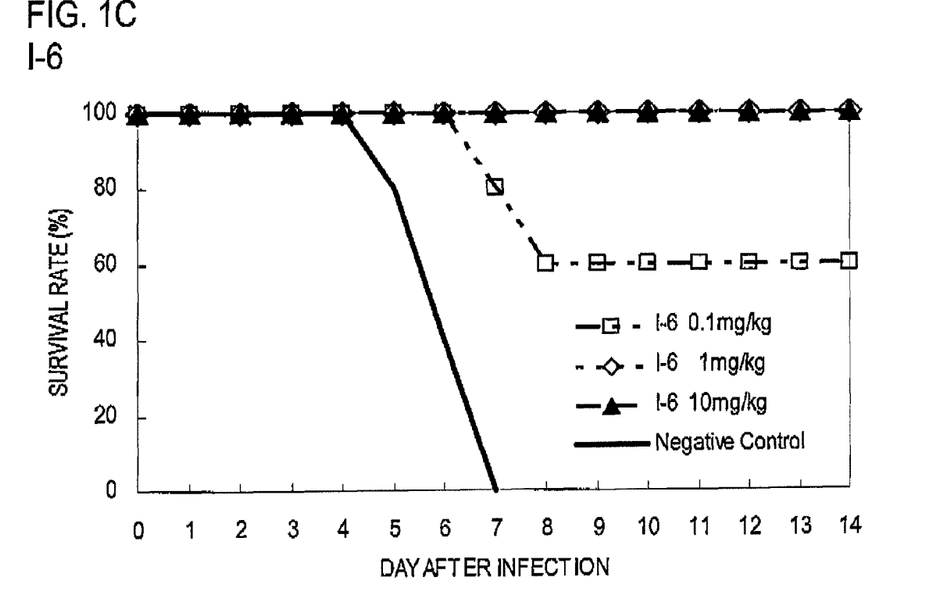
Figure 1D:
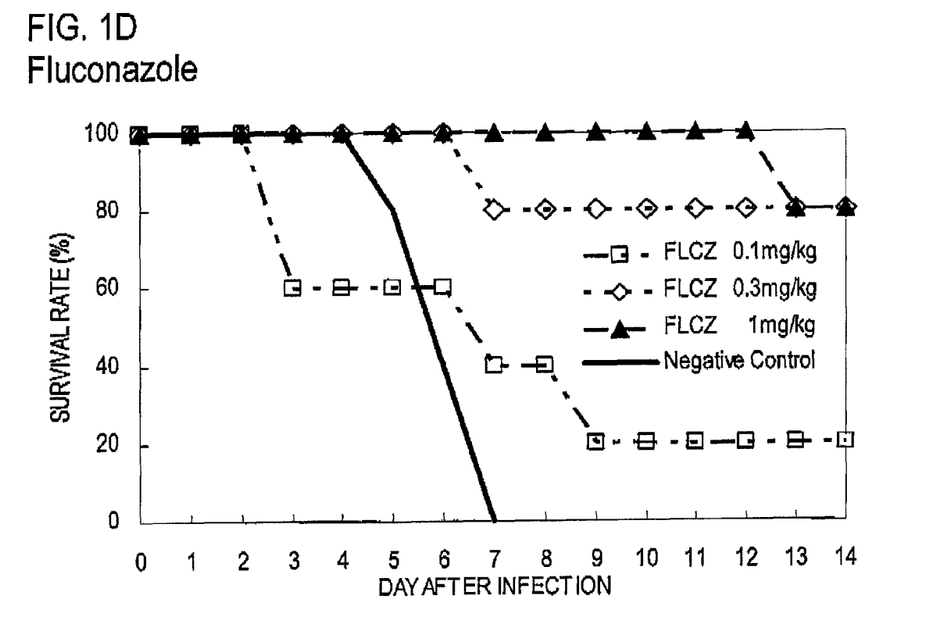

The results were shown in Table 3 below and FIGS. 1A to 1D. In the table, the administration dose of the compounds of the present invention and the comparative compound represents a mg amount per 1 kg of a mouse weight (mg/kg).

Significant deference was tested, by 5% for both sides of the levels of significance, in accordance with the Kaplan-Meier method Logrank test (comparison of multiple groups), on the survival time distribution of each of the substances to be tested and control substance administration groups and sterile physiological saline administration group. SAS release 8.2 (SAS Institute Japan) was used in the Kaplan-Meier method Logrank test. (T/C(%)=[survival time of administration group (integrated value)/survival time of control group (integrated value)]×100)

TABLE 3

| day | I-3 (mg/kg) | | | I-1 (mg/kg) | | | I-6 (mg/kg) | | | FLCZ (mg/kg, s.c.) | | | Negative Control |
|---|---|---|---|---|---|---|---|---|---|---|---|---|---|
| | 0.1 | 1 | 10 | 0.1 | 1 | 10 | 0.1 | 1 | 10 | 0.1 | 0.3 | 1 | |
| 0 | 100 | 100 | 100 | 100 | 100 | 100 | 100 | 100 | 100 | 100 | 100 | 100 | 5 |
| 1 | 100 | 100 | 100 | 100 | 100 | 100 | 100 | 100 | 100 | 100 | 100 | 100 | 5 |
| 2 | 100 | 100 | 100 | 100 | 100 | 100 | 100 | 100 | 100 | 100 | 100 | 100 | 5 |
| 3 | 60 | 80 | 60 | 60 | 100 | 60 | 100 | 100 | 100 | 60 | 100 | 100 | 5 |
| 4 | 60 | 80 | 60 | 60 | 100 | 60 | 100 | 100 | 100 | 60 | 100 | 100 | 5 |
| 5 | 60 | 60 | 60 | 60 | 80 | 60 | 100 | 100 | 100 | 60 | 100 | 100 | 4 |
| 6 | 60 | 40 | 60 | 60 | 80 | 60 | 100 | 100 | 100 | 60 | 100 | 100 | 2 |
| 7 | 40 | 40 | 40 | 20 | 60 | 40 | 80 | 100 | 100 | 40 | 80 | 100 | 0 |
| 8 | 40 | 40 | 20 | 20 | 60 | 40 | 60 | 100 | 100 | 40 | 80 | 100 | — |
| 9 | 40 | 40 | 20 | 20 | 60 | 40 | 60 | 100 | 100 | 20 | 80 | 100 | — |
| 10 | 40 | 40 | 20 | 20 | 40 | 40 | 60 | 100 | 100 | 20 | 80 | 100 | — |
| 11 | 40 | 40 | 20 | 20 | 40 | 40 | 60 | 100 | 100 | 20 | 80 | 100 | — |
| 12 | 40 | 40 | 20 | 0 | 40 | 40 | 60 | 100 | 100 | 20 | 80 | 100 | — |
| 13 | 40 | 40 | 20 | — | 20 | 20 | 60 | 100 | 100 | 20 | 80 | 80 | — |
| 14 | 40 | 40 | 20 | — | 20 | 20 | 60 | 100 | 100 | 20 | 80 | 80 | — |
| T/C(%) | 139 | 142 | 116 | 103 | 161 | 132 | 194 | 242 | 242 | 119 | 216 | 235 | 100 |

It is evident from the above-mentioned results that the compounds of the invention have excellent antifungal action and are particularly effective for *Candida*. The compounds of the invention are useful as superior antifungal therapeutic agents.

A novel triazole derivative having an antifungal action is provided by the invention.

This application is based on Japanese patent application JP 2008-143232, filed on May 30, 2008, the entire content of which is hereby incorporated by reference, the same as if set forth at length.

What is claimed is:

1. A triazole derivative represented by formula (I) or pharmaceutically acceptable salt thereof;

(I)

wherein,
* represents an asymmetric carbon and takes R configuration or S configuration; and
R1 represents a structure represented by formula (II) or (III):

(II)

(III)

----- represents single bond or double bond
wherein,
Y represents a hydrogen atom or an oxygen atom; and
R2 and R3 each independently represent a hydrogen atom, an alkyl group, an aryl group, an alkoxy group, a formyl group, a carboxyl group, an alkylcarbonyl group, an arylcarbonyl group, an alkoxycarbonyl group, a carbamoyl group, an amino group, an alkylcarbonylamino group, an arylcarbonylamino group, a cyano group, a nitro group or a halogen atom.

2. The triazole derivative or pharmaceutically acceptable salt thereof according to claim 1, wherein R2 represents a hydrogen atom, an alkyl group having from 1 to 8 carbon atoms, an alkoxyl group having from 1 to 8 carbon atoms, a cyano group or a halogen atom; and
R3 represents a hydrogen atom, an alkyl group having from 1 to 8 carbon atoms, an alkoxyl group having from 1 to 8 carbon atoms, a cyano group or a halogen atom.

3. The triazole derivative or pharmaceutically acceptable salt thereof according to claim 2,
wherein R2 represents a hydrogen atom, an alkyl group having from 1 to 4 carbon atoms, a cyano group, a chlorine atom or a fluorine atom; and
R3 represents a hydrogen atom, an alkyl group having from 1 to 4 carbon atoms, an alkoxyl group having from 1 to 4 carbon atoms, a cyano group, a chlorine atom or a fluorine atom.

4. The triazole derivative or pharmaceutically acceptable salt thereof according to claim 3,
wherein R2 represents a hydrogen atom ox a methyl group; and
R3 represents a hydrogen atom, an alkyl group having from 1 to 4 carbon atoms, a chlorine atom or a fluorine atom.

5. The triazole derivative or pharmaceutically acceptable salt thereof according to claim 1,
wherein the triazole derivative represented by formula (I) is a structure represented by formula (I'):

(I')

wherein R1 has the same meaning as R1 in formula (I).

6. The triazole derivative or pharmaceutically acceptable salt thereof according to claim 1,
wherein R1 represents a structure represented by formula (III-1) or (III-2):

(III-1)

(III-2)

wherein R2 and R3 in formulae (III-1) and (III-2) are the same as R2 and R3 in formulae (II) and (III).

7. A pharmaceutical composition, comprising:
the triazole derivative or pharmaceutically acceptable salt thereof according to claim 1.

* * * * *